(12) United States Patent
Veasey et al.

(10) Patent No.: US 7,001,360 B2
(45) Date of Patent: Feb. 21, 2006

(54) MEDICAMENT INJECTION DEVICE

(75) Inventors: Robert Frederick Veasey, Warwickshire (GB); James Alistair Holdgate, Warwickshire (GB)

(73) Assignee: DCA Design International Limited, Warwick (GB)

( * ) Notice: Subject to any disclaimer, the term of this patent is extended or adjusted under 35 U.S.C. 154(b) by 248 days.

(21) Appl. No.: 10/347,702

(22) Filed: Jan. 22, 2003

(65) Prior Publication Data

US 2004/0087903 A1 May 6, 2004

(30) Foreign Application Priority Data

Jan. 25, 2002 (GB) .................................. 0201689

(51) Int. Cl.
*A61M 37/00* (2006.01)
(52) U.S. Cl. ..................................... 604/155; 604/131
(58) Field of Classification Search ................ 604/131, 604/139, 151, 154, 155, 224, 232
See application file for complete search history.

(56) References Cited

U.S. PATENT DOCUMENTS

| | | | |
|---|---|---|---|
| 4,585,439 A | | 4/1986 | Michel |
| 5,279,585 A | * | 1/1994 | Balkwill ..................... 604/207 |
| 5,304,152 A | * | 4/1994 | Sams .......................... 604/207 |
| 5,674,204 A | * | 10/1997 | Chanoch ..................... 604/211 |
| 5,690,618 A | | 11/1997 | Smith et al. |
| 6,221,046 B1 | * | 4/2001 | Burroughs et al. ......... 604/153 |

| | | | |
|---|---|---|---|
| 2001/0023637 A1 | | 9/2001 | Klitmose et al. |
| 2002/0029018 A1 | * | 3/2002 | Jeffrey ........................ 604/209 |

FOREIGN PATENT DOCUMENTS

| | | |
|---|---|---|
| EP | 0 143 895 A1 | 6/1985 |
| EP | 0 688 571 A1 | 12/1995 |
| EP | 1 095 668 A1 | 5/2001 |
| FR | 2 598 624 | 11/1987 |
| WO | WO 89/11310 | 11/1989 |
| WO | WO 93/02720 A1 | 2/1993 |
| WO | WO 98/47552 | 10/1998 |
| WO | WO 01/17593 A1 | 3/2001 |

* cited by examiner

*Primary Examiner*—Sharon Kennedy
(74) *Attorney, Agent, or Firm*—Oliff & Berridge, PLC

(57) ABSTRACT

The present invention relates to a medicament delivery device in which the medicament to be delivered is stored within a cartridge having a displaceable piston therein. The displaceable piston is driven to expel medicament by way of a lead screw that is advanced and retracted by way of a suitable drive mechanism. A guideway through which the lead screw travels is provided. However, in known devices the guideway is held in position by other components of the apparatus. Such devices can be complex to manufacture. Also they may require disassembly and reassembly when a cartridge is to be replaced. This is a disadvantage if the user, as is common amongst those with diabetes, is infirm or has impaired vision. A medicament delivery device is disclosed comprising a main housing, a threaded lead screw having opposing flat surfaces, rotary driving means having inner wall surfaces corresponding to the opposing flat surfaces of the lead screw and a guide housing having an opening through which the threaded lead screw is received in which the guide housing is permanently fixed to the main housing.

4 Claims, 4 Drawing Sheets

MEDICAMENT INJECTION DEVICE

The present invention relates to a medicament delivery device such as an injection or infusion device. In particular, this invention has particular, but not exclusive, application to a medicament delivery device in which the medicament to be delivered is stored within a replaceable cartridge having a displaceable piston therein. Such devices are, for example, commonly used by those with diabetes for the administration of insulin.

In such devices the displaceable piston is driven to cause medicament to be expelled by way of a lead screw or other plunger. The lead screw may conveniently be advanced and retracted by way of a suitable drive mechanism. It is known to provide a drive mechanism in which the rotary movement of a motor or other suitable drive means is transformed into linear movement of the lead screw.

It is known to provide a guideway or guide housing through which the lead screw travels. However, in known devices the guideway is held in the desired operating position by other components of the apparatus.

For example, in EP 0 143 895 there is disclosed an infusion device. The device comprises a housing having a shaped cavity formed therein. A first part of the cavity serves as a mounting support for a replaceable medicament cartridge. A rotatable driver sleeve is located in a second part of the cavity. The lead screw is adapted to travel through the driver sleeve. The threaded lead strew has opposing flat surfaces. The inside of the carrier sleeve conforms to the shape of the lead screw to prevent rotation of the lead screw independently of the driver sleeve. The guideway takes the form of a threaded nut threaded onto the lead screw. The nut is located in a specially shaped locating recess of the housing cavity to prevent rotation of the nut. Axial movement of the nut is prevented because in use, the nut is trapped between on one side the housing and on the other by one end of the medicament cartridge cylinder. In use, the driver sleeve carries along the threaded rod that moves ahead as a screw spindle through the nut or guideway held in the housing.

Such devices are complex to manufacture. The shaped cavity requires a suitable tolerance both correctly to receive the driver sleeve and to provide a suitably shaped locating recess for the nut acting as a guideway. In addition, correct location of the cartridge cylinder is required to prevent the out from becoming loose and the correct location of the nut must be ensured every time that a medicament cartridge is replaced. Such disassembly and reassembly when a cartridge is to be replaced is a disadvantage if the user, as is common amongst those with diabetes, is infirm or has impaired vision.

The use of guide means is also known in medicament delivery devices in which linear displacement of an actuator causes, directly or indirectly, linear motion of a lead screw along a longitudinal axis to cause a medicament to be dispense. In such devices the travel of the lead screw is limited by displaceable guide means, the displacement of the guide means corresponding to a dosage selected by a user.

In such an injector, a lead screw having flat opposite sides is again located within a driver. The driver interacts with a nut. The nut has an opening shaped to receive the lead screw so as to prevent the lead screw from rotating with respect to the nut. The nut has splines that releasably engage with splines on a body portion of the pen. A retainer is also releasably mounted to the body to retain a medicament cartridge in place. When the cartridge is absent, the retract nut and the lead screw are free to rotate and to backdrive into the body. However, a snap ring is required to hold the nut captive on the driver to prevent it from spinning down the lead screw when a cartridge is changed.

There is a need for a medicament delivery device that removes or at least reduces these problems.

According to the present invention, a medicament delivery device comprises a main housing, a threaded lead screw having opposing flat surfaces, rotary driving means having inner wall surfaces corresponding to the opposing flat surfaces of the lead screw and a guide housing having an opening through which the threaded lead screw is received in which the guide housing is permanently fixed to the main housing.

This has as an advantage that the guide housing cannot become displaced in relation to the lead screw.

Preferably, the guide housing is formed integrally with the main housing.

Preferably, the main housing comprises two half shells and a guide housing unit in which the guide housing is formed. More preferably, a motor and a plurality of rotary driving means are carried from the guide housing unit.

The invention will now be described, by way of example only, with reference to the accompanying drawings in which.

Figure 1:
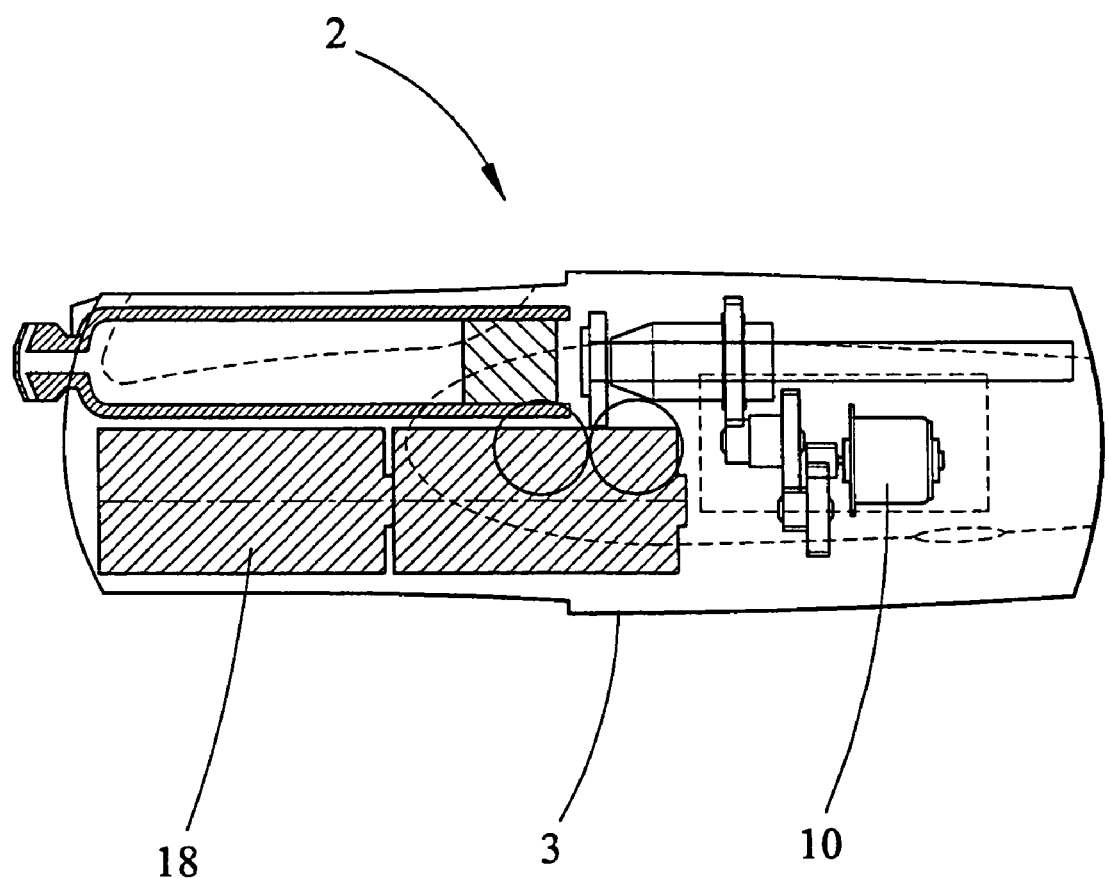
FIG. 1 shows somewhat schematically a medicament delivery device in accordance with the present invention with elements of the main housing shown in ghost.
Figure 2:
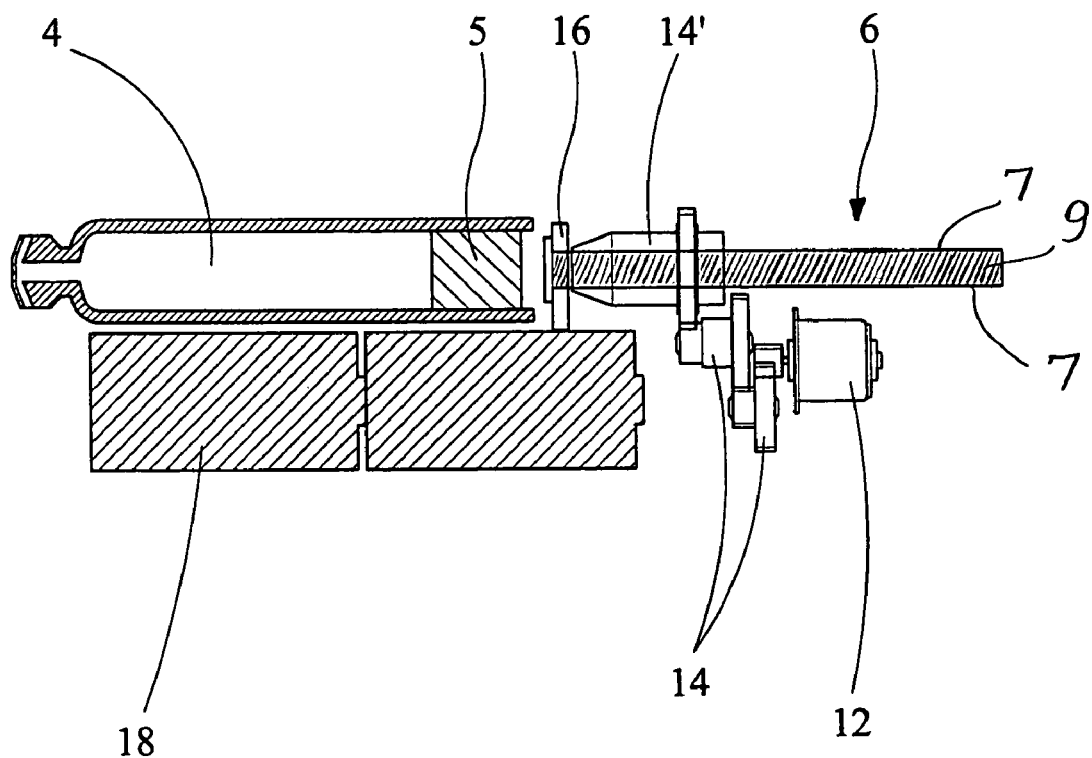
FIG. 2 shows a similar view to that of FIG. 1 with much of the main housing removed for reasons of clarity.
Figure 3:
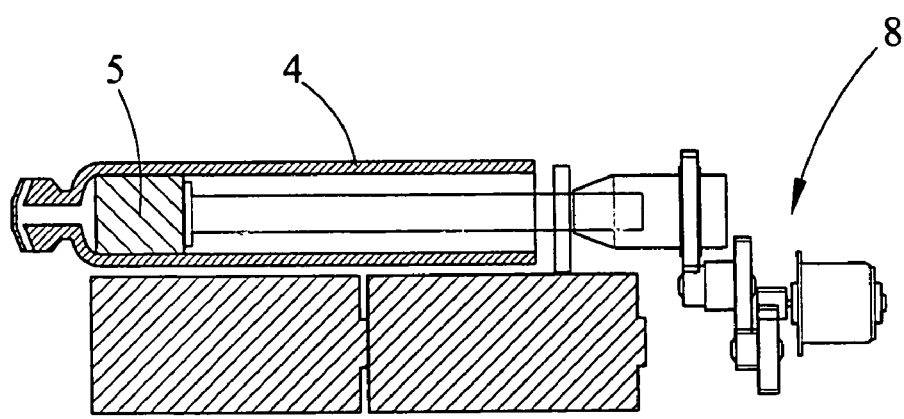
FIG. 3 shows a view similar to that of FIG. 2 with the lead screw in an advanced position.
Figure 4:
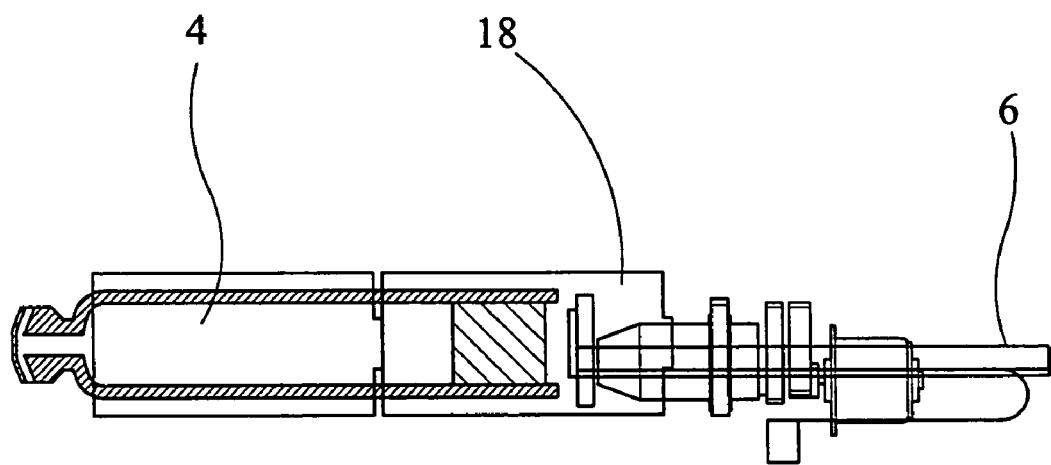
FIG. 4 shows a side view corresponding to FIGS. 1 and 2, again with much of the main housing removed for clarity.
Figure 5:
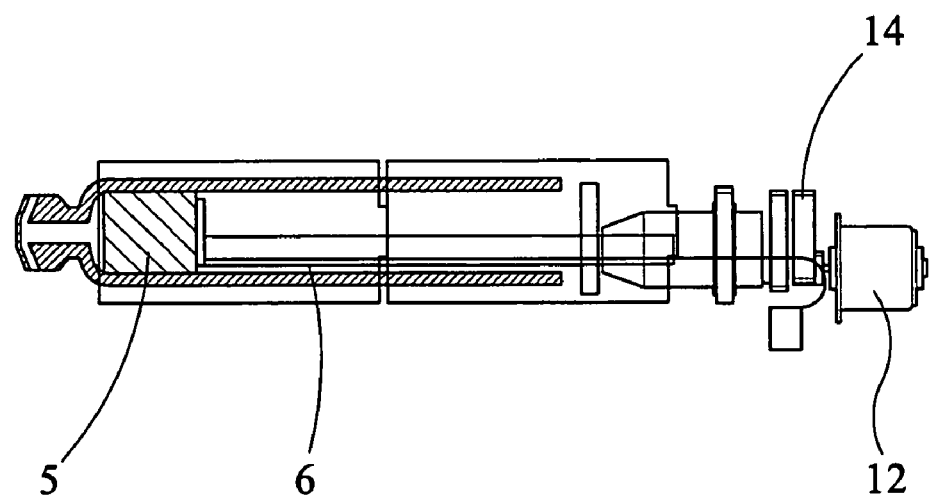
FIG. 5 shows a side view similar to FIG. 4 with the lead screw in an advanced position in line with FIG. 3.

Referring to the FIGS. 1 to 5 generally, and FIG. 1 in particular, there is shown a medicament delivery device 2 comprising a main housing 3 within which are located a number of components including a replaceable medicament cartridge 4, a plunger in the form of a lead screw 6 to drive a piston 5 within the medicament cartridge 4 to cause in use the medicament to be expelled and drive means 8 to drive the plunger. A power source such as batteries 18 may also be provided to power the drive means 8. The medicament delivery device 2 may also include a display 10 by which certain information relevant to the operation and/or use of the medicament delivery device may be communicated to a user.

A central control unit or microprocessor (not shown) may also be provided to control operation of the medicament delivery device 2 and to determine the nature of the information appearing upon the display 10.

The plunger and drive means are shown most clearly in FIGS. 2 to 5. A motor 12 is connected to drive the lead screw 6 or plunger by way of a number of rotary driving means such as drive train elements 14,14' disposed to form a drive train. The lead screw 6 is typically of generally circular section though having oppositely disposed flat sides 7 extending axially of the lead screw. A screw thread 9 is carried by the remaining sides of the lead screw 6. The lead screw 6 is disposed to operate through a guide housing 16. The guide housing 16 is formed as a part of the main housing 3. The guide housing 16 includes an opening through which the lead screw 6 passes. The opening of the guide housing 16 is configured to the cross-section of the lead screw 6 to prevent relative rotation between the lead screw 6 and the guide housing 16.

A final element 14' in the gear train is provided with a threaded bore through which the lead screw 6 also passes. This final gear train element 14' is permitted to rotate with respect to the lead screw 6. When driven by the other elements 14 in the drive train, rotation of the final gear train element 14' in the drive train causes the lead screw 6 which is unable to rotate due to the guide housing to process therethrough. In this way by controlling the direction of rotation of the final gear train element 14', the lead screw 6 may either be advanced through the replaceable medicament cartridge 4 to dispel medicament or retracted to facilitate the subsequent insertion of a replacement medicament cartridge 4.

The main housing 3 is normally formed as two opposing half shells. The guide housing 16 may be formed integrally with one of the half shells. Alternatively, the guide housing 16 may be formed in portions on each half shell to form a completed guide housing 16 when the main housing 3 is assembled. As a further alternative the guide housing 16 may be affixed to one of the half shells prior to assembly of the medicament delivery device 2.

Figure 6:
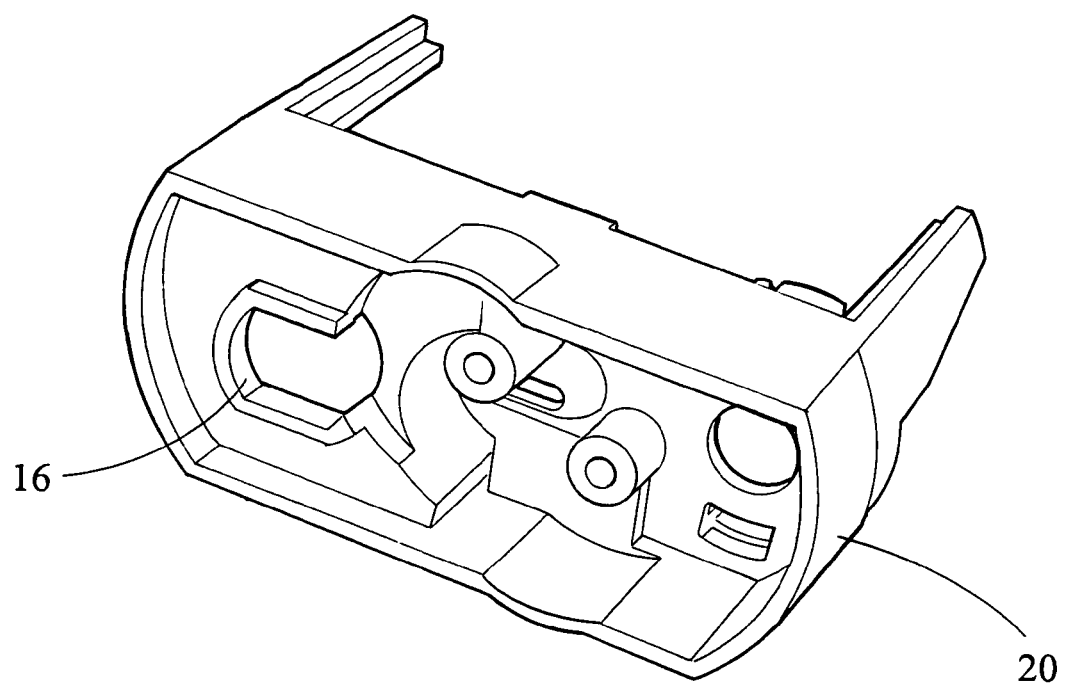
FIG. 6 shows a boy unit in which a guide housing has been formed.

As a further alternative, where the guide housing is formed integrally with the main housing, that part of the main housing may be formed as a separate unit 20 (FIG. 6) for location between two opposing half sells, that is the main housing 3 comprises the two opposing half shells and the guide housing unit 20, the remaining components being disposed in relation to these elements of the main housing. For example, the drive train elements 14,14' and the motor 12 may conveniently be mounted to the guide housing unit 20.

What is claimed is:

1. A medicament delivery device comprising:
   a main housing,
   a motor,
   a threaded lead screw having opposing flat surfaces,
   rotary driving means, and
   a guide housing having an opening configured to a cross section of the lead screw so as to prevent relative rotation between the lead screw and the guide housing, the guide housing being permanently fixed to the main housing,
   wherein the motor drives the lead screw through a plurality of the rotary driving means and the motor and the plurality of rotary driving means are carried from the guide housing unit.

2. The medicament delivery device according to claim 1, in which the guide housing is formed integrally with the main housing.

3. The medicament delivery device according to claim 2, in which the main housing comprises two half shells and a guide housing unit in which the guide housing is formed.

4. The medicament delivery device according to claim 1, wherein the plurality of the rotary driving means comprises a plurality of drive train elements.

* * * * *